United States Patent [19]

Mauze et al.

[11] Patent Number: 5,154,890

[45] Date of Patent: Oct. 13, 1992

[54] FIBER OPTIC POTASSIUM ION SENSOR

[75] Inventors: Ganapati R. Mauze, Sunnyvale, Calif.; Lothar Rupp, Aixheim, Fed. Rep. of Germany

[73] Assignee: Hewlett-Packard Company, Palo Alto, Calif.

[21] Appl. No.: 610,289

[22] Filed: Nov. 7, 1990

[51] Int. Cl.$^5$ .................. G01N 21/64; G01N 33/20; A61B 5/00

[52] U.S. Cl. ............... 422/82.07; 422/82.05; 422/82.06; 422/82.08; 128/634; 356/39; 436/79; 436/805; 549/352

[58] Field of Search .............. 128/634; 356/39; 549/351, 352; 422/82.05–82.08; 436/74, 79, 805

[56] References Cited

U.S. PATENT DOCUMENTS

| | | | |
|---|---|---|---|
| 4,367,072 | 1/1983 | Vögtle et al. | 436/805 X |
| 4,499,052 | 2/1985 | Fulwyler | 422/82.08 X |
| 4,582,809 | 4/1986 | Block et al. | 422/82.05 X |
| 4,649,123 | 3/1987 | Charlton et al. | 436/74 X |
| 4,739,081 | 4/1988 | Toke et al. | 549/351 |
| 4,762,799 | 8/1988 | Seitz et al. | 422/82.07 X |
| 4,892,640 | 1/1990 | Wolfbeis et al. | 250/459.1 X |
| 4,925,268 | 5/1990 | Iyer et al. | 422/82.07 X |
| 5,019,350 | 5/1991 | Rhum et al. | 422/82.07 |
| 5,037,615 | 8/1991 | Kane | 128/634 X |

FOREIGN PATENT DOCUMENTS 0143564  6/1985  European Pat. Off. ............ 549/351

OTHER PUBLICATIONS

Tarcali et al. "In Vivo Measurement with a Potassium Ion-Selective Microelectrode Base a New Bis(Crown Ether)" *Anal. Chim. Acta*, 1985, 178, 231–237.

Gehrich et al. "Optical Fluorescence and Its Application to an Intravascular Blood Gas Monitoring System" *IEEE Trans. Biomedical Engineering*, 1986, BME-33, 117–131.

Wolfbeis et al. "Optical Sensors: An Ion-Selective Optrode for Potassium", *Anal. Chim. Acta*, 1987, 198, 1–12.

*Primary Examiner*—James C. Housel
*Assistant Examiner*—Arlen Soderquist

[57] ABSTRACT

A sensor (10) is provided for detecting the concentration of potassium ions which comprises a molecule which selectively complexes potassium ions. The molecule, e.g., 2,2-bis(3,4-(15-crown-5)-2-nitrophenylcarbamoxymethyl)tetradecanol-14, has at least one binding site and is provided with a fluorophore group, e.g., Rhodamine-B, at that site. The molecule is one that expands upon complexation of potassium ions, such that the intensity of fluorescence increases. The change in fluorescent intensity is a direct measure of the concentration of potassium ions. A detector employing the sensor is also provided.

12 Claims, 3 Drawing Sheets

FIBER OPTIC POTASSIUM ION SENSOR

TECHNICAL FIELD

The present invention relates to sensors, and more particularly, to a sensor that can selectively recognize and transduce the change in potassium ion concentration into a measurable optical signal.

BACKGROUND ART

Monitoring of blood levels of potassium ion concentration is of considerable importance in intensive care medicine. Currently, the measurement is done in a clinical chemistry lab from blood samples drawn at frequent intervals. Although this technique is satisfactory in many situations, very often life-threatening episodes of potassium shift may not be detected by such an intermittent technique. Again, in some patients frequent blood sampling is not desired due to anemic conditions. The need for a continuous real-time monitoring has provided considerable impetus for the development of a new modality for potassium measurement.

Early attempts at designing an in-dwelling sensor for potassium measurement were directed at modifying the potassium electrodes used in the clinical lab machines. However, the possibility of electrical hazard, instability due to the extremely corrosive nature of blood, and need for a reference electrode have seriously hampered progress in this field. Thus, in spite of being relatively older technology, electrodes have found very few applications in in vivo sensors.

More recently, fiber-optic sensors have been developed for in vivo measurement of pH, $pCO_2$, and $pO_2$. Important advantages of the optical approach are stability with respect to calibration, absence of electrical hazard and the relative ease of miniaturization. Accordingly, attempts have been made to develop fiber-optic sensors for in vivo measurement of alkali metal ions. Fluorescent probes made by fusing ion selective cryptands with 4-methyl-coumarin dyes are known. However, this scheme is not reversible and therefore not useful for continuous measurements.

Wolfbeis et al, in *Analytica Chemica Acta*, Vol. 198, pp 1–12 (1987), have described a probe consisting of rhopp. damine ester as a fluorophore and valinomycin as an ionophore. Zhujun and Seitz, in SPIE, "Optical Fibers in Medicine III" Vol. 906, pp. 74–79 (1988), have described a similar probe using merocyanine 540 as a fluorophore instead of rhodamine ester. All these schemes appear to be in their experimental stage and have not demonstrated stable sensitivity and amenability to miniaturization. Further, they consist of a Langmuir-Blodgett film, which cannot maintain structural integrity under the conditions of in vivo application. Finally, it is not clear how these schemes could be adopted for fiber optic configurations.

It is clear, however, that there is a need for a potassium sensor for real-time monitoring of potassium ion levels in blood.

DISCLOSURE OF INVENTION

In accordance with the invention, a sensor is provided for detecting the concentration of potassium ions. The sensor permits transducing the changes in the potassium ion concentration into a corresponding change in the fluorescent signal emitted by a fluorophore immobilized in a ion permeable polymer matrix containing an ion-selective ionophore. The components of the sensor described herein are chosen so as to allow easy miniaturization and adoption in the existing modality for real time in vivo measurement of blood parameters such as pH, $pCO_2$, $pO_2$, and arterial pressure. However, the technique is applicable for any application of ion measurements.

A detector employing the sensor of the invention comprises (a) a source of electromagnetic radiation, (b) the sensor, and (c) means for measuring any change in intensity of said radiation passed through said sensor.

The sensor of the invention avoids the problems associated with earlier potassium probes, and is not affected by the corrosive nature of blood, nor is it of an unsuitably large size. Finally, the sensor of the invention avoids any electrical hazard.

In addition to all the advantages of an optical system mentioned above some of the specific advantages of this invention are:

(1) The sensing system is easily adaptable for small in-dwelling sensors with fiber-optic connections to store and display the continuous variation of the ion concentration by the patient bedside.

(2) The optical range in which the sensor operates is in the green to red portion of the visible light spectrum. This permits the use of inexpensive and low power-consuming solid state light sources and detectors along with inexpensive commercial grade optical fibers. Thus, the sensor itself can be made to be disposable after being used on a single patient. Moreover, the low power requirements allow design of a battery-operated system which can be portable and used with ambulatory equipment.

BEST MODES FOR CARRYING OUT THE INVENTION

The mechanism of potassium ion sensing can be explained as a two-step process. The first step involves selectively recognizing potassium ions. The second step involves changing the fluorescence of a fluorophore in a one-to-one correspondence with the concentration of potassium ions in a solution to which the sensor is exposed. In this invention, the two steps are combined in a novel way. The selectivity to potassium ion is achieved by using an ionophore which has excellent selectivity to potassium ions. The preferred ionophore is 2,2-bis[3,4-(15-crown-5)-2-nitrophenylcarboxy-methyl]-tetradecane (BME-44):

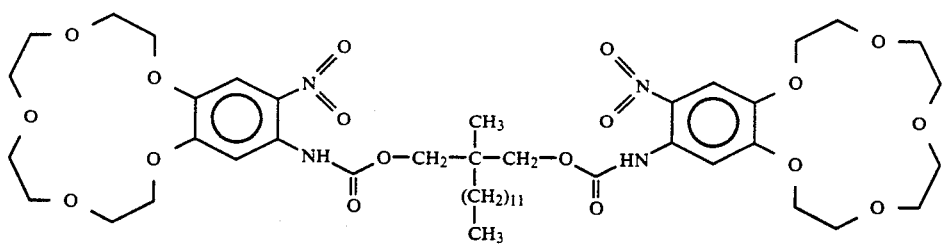

Other suitable ionophores employed in the practice of the invention include Valinomycin, 18-Crown-6, derivatives thereof, and the like.

In the process of selectively binding potassium ions, the bis-crown ether causes a local charge separation (of the potassium cation and its counterion). This disturbs the local electrical potential. In this invention, this change in electrical potential is sensed optically by a potential sensitive fluorophore, Rhodamine-B:

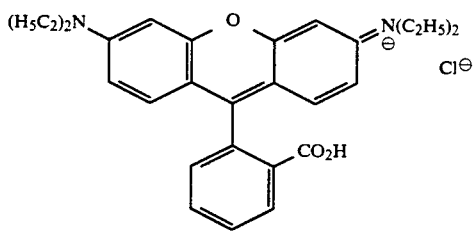

Other suitable fluorophores employed in the practice of the invention include Rhodamine-110, Fluorescein, 2,7'-dichlorfluorescein, and the like.

Figure 1A:
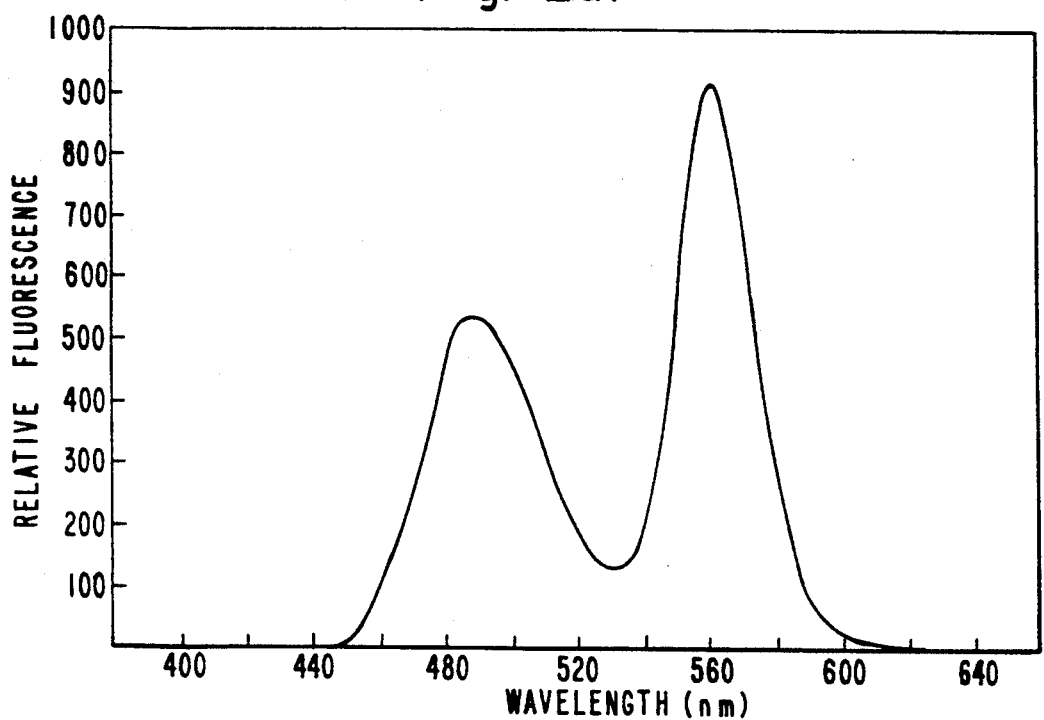
FIG. 1A, on coordinates of relative fluorescence and wavelength, is a plot of the excitation spectrum of Rhodamine-B.
Figure 1B:
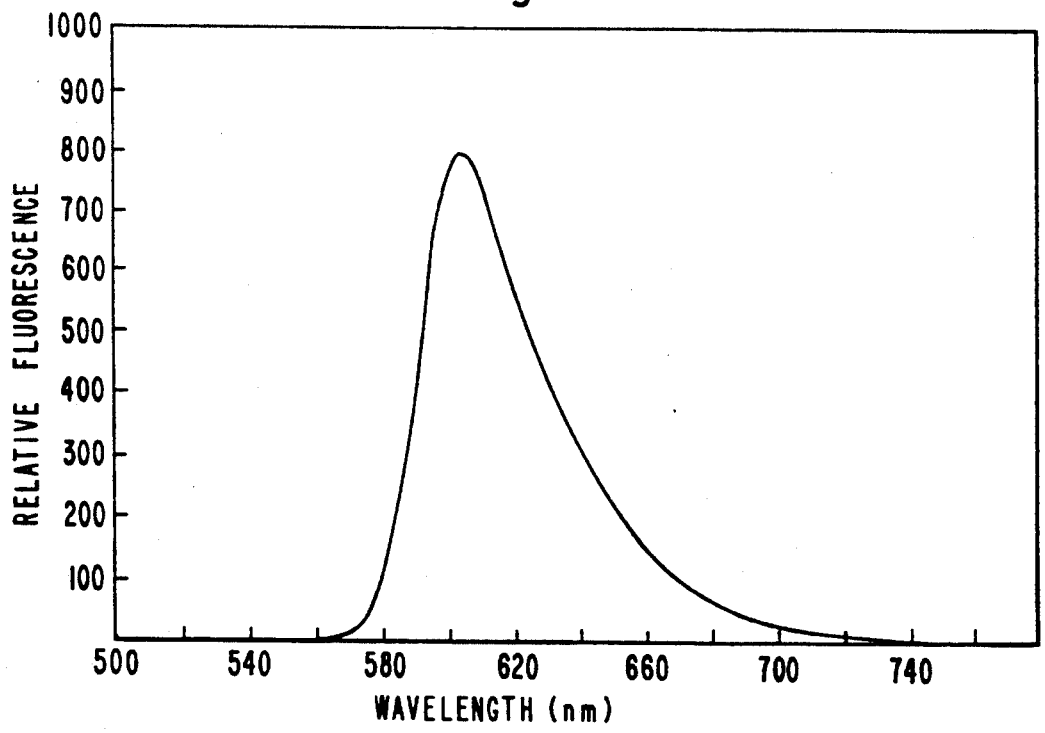
FIG. 1B, on the same coordinates as FIG. 1A, is a plot of the emission spectrum of Rhodamine-B.

Rhodamine-B has an excitation maximum in the green part of the visible spectrum and a fluorescence maximum in the red part (see FIGS. 1A and 1B). Changes in the electronic ambient of this fluorophore changes the amount of fluorescence emitted.

In accordance with the invention, Rhodamine-B is bound to BME-44 and immobilized in a hydrophilic polymer. In the presence of a potassium ion, the lyophilic group linking the two 15-crown-5 groups folds such that a hydrogen bond is formed between 0 of NO, near one crown group and H of NH group near the other crown group. The folding of the two 15-crown-5 groups has been described by J. Tarkali et al, in Analytica Acta, Vol. 178, pp. 231-237 (1985).

The two crown groups then align over each other in such a way as to form a sandwich complex with the potassium ion. The conformational changes and the bond distances in the complex are such that these are possible only in the presence of a potassium ion, other ions being either too large or unable to form the required number of bonds for the complex formation. Thus, the potential changes near the Rhodamine-B molecules are exclusively due to the binding of potassium ions. This leads to changes in fluorescence of Rhodamine-B that are specifically due to potassium ions.

In the ionophore, only the crown, NH—C=O and $NO_2$ groups take part in the ion recognition process. The lyophilic group takes part in the chain folding, but the groups attached to the central carbon atom in this molecule do not participate in any of these steps. Also, these groups do not physically interfere with these steps for they lie in a totally different plane. For these reasons, they serve as ideal locations to attach the fluorophores such as Rhodamine-B.

Figure 2:
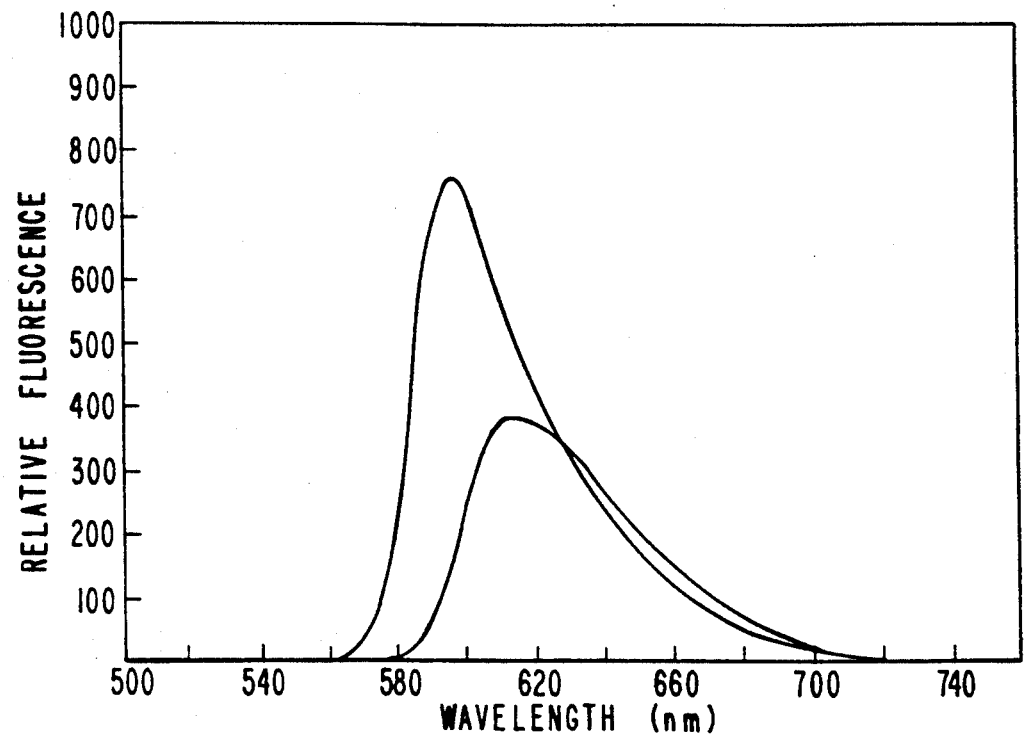
FIG. 2, on the same coordinates as FIG. IA, is a plot of the emission spectrum of Rhodamine-B with BME-44 (an ionophore used in the practice of the invention) in $H_2O$ and 100 mM KCl.
Figure 3:
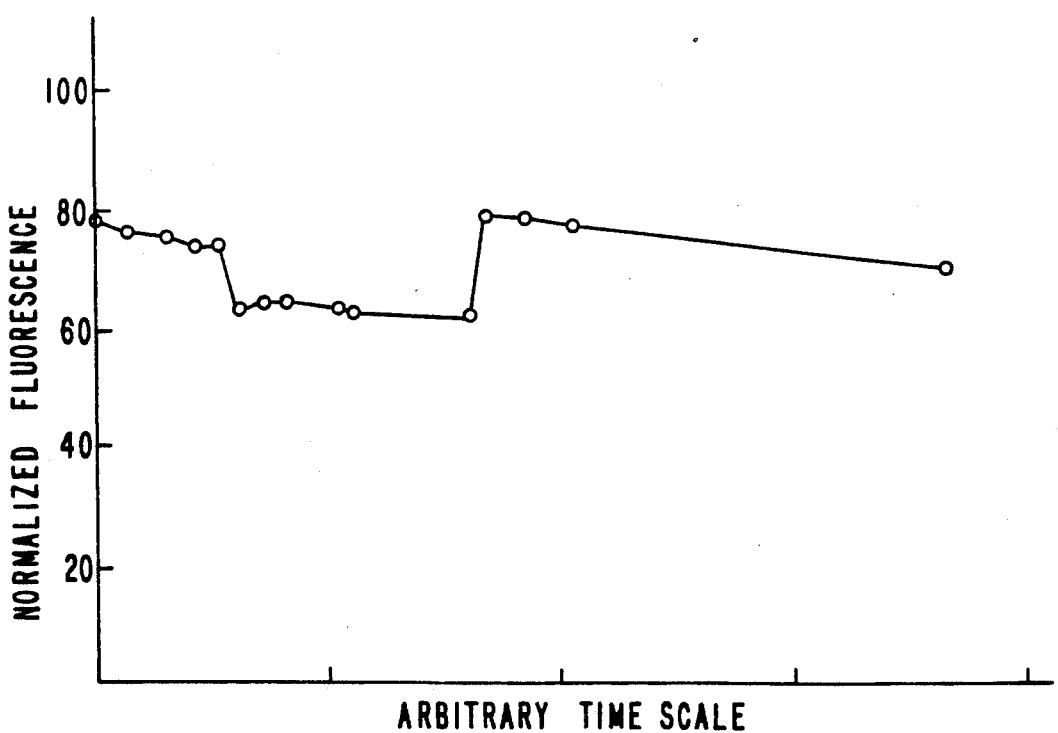
FIG. 3, on coordinates of normalized fluorescence and time, depicts the fluorescence response of Rhodamine-B with BME-44 trapped in a PVC matrix with a plasticizer.

When an ionophore thus tagged with a fluorophore binds a potassium ion, the presence of a localized charge alters the potential distribution in the vicinity of the fluorophore. This greatly affects the fluorescence emitted by the fluorophore. FIG. 2 shows a typical change in the fluorescence spectrum of Rhodamine-B which is trapped in an organic phase along with BME-44 and then exposed to aqueous solutions. FIG. 3 shows the changes in the fluorescence emitted by Rhodamine-B trapped in a polyvinyl chloride membrane along with BME-44 and a plasticizer when this membrane is exposed to different potassium ion concentrations. It will be appreciated by those skilled in this art that this demonstrates the feasibility of the scheme described above. The drift in FIG. 3 is due to the fact that the crown ether was not immobilized and thus was continuously being lost during the measurements. In a stable form of the sensor, the three components will be immobilized together as described earlier.

Synthesis of Potassium Sensitive Gel:

The reaction schemes used for binding BME-44 to Rhodamine-B (as an ester) and then immobilizing it in a polyacrylamide gel is described below:

A. Synthesis of BME-44 with OH group at the end of the $(CH_2)_{12}$ group (Hydroxy-BME-44) (on the fourteenth carbon atom of the chain):

Step 1: Synthesis of 4-nitro(15-crown-5)-3-phenyliosicyanate

The starting material was a benzo-15-crown-5 compound (Aldrich 28,279-0) (I) which was nitrated according to the procedure by R. Ungaro et al., Journal of the American Chemical Society. Vol. 98, pp. 5198-5202 (1976):

To the benzo-15-crown-5 (I) dissolved in a mixture of chloroform and acetic acid was added 70% nitric acid. The mixture was stirred for 24 hours at room temperature, then neutralized with aqueous sodium carbonate and the chloroform layer separated. The aqueous layer is extracted with chloroform and the combined chloroform extracts are dried over magnesium sulfate. After evaporation of the solvent and recrystallization from ethanol, a pure compound (II) was obtained (yield: 85%).

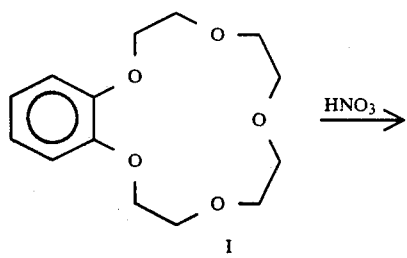

I

HNO₃ →

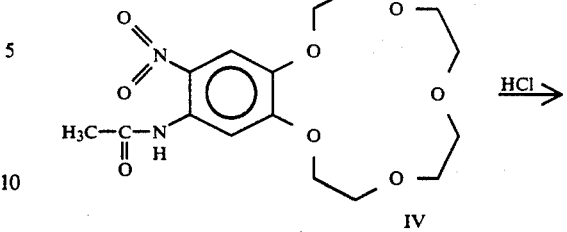

IV

HCl →

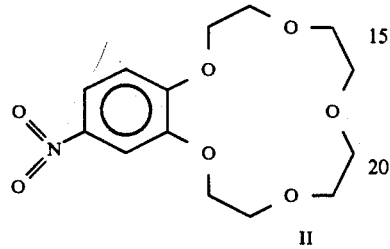

II

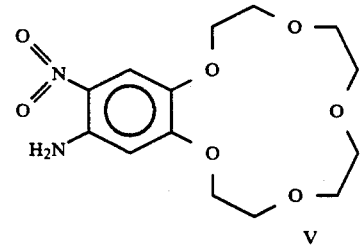

V

This nitrobenzo-15-crown-5 (II) was reduced and nitrated by catalytic hydrogenation according to L. Toke et al., *Liebigs Annalen der Chemie*, 349–353 (1988):

A methanol/water solution of 4-nitrobenzo-15-crown-5 (II) was hydrogenated at 50 atm. hydrogen pressure in the presence of Raney Ni. After filtering off the catalyst, the mother liquor was evaporated to dryness, the oily residue (III) was mixed with glacial acetic acid and acetic anhydride and nitrated with nitric acid (70%) below 60° C. The reaction mixture was poured into ice/water, and 3-acetylamino-4-nitrobenzo15-crown-5 (IV), which was obtained as a precipitate, was hydrolyzed in boiling aqueous HCl (18%), obtaining 3-amino-4-nitrobenzo-15-crown-5 (V) by neutralization with sodium carbonate. A very pure yellow product was obtained by chromatography on silica with chloroform as solvent (yield: 11%).

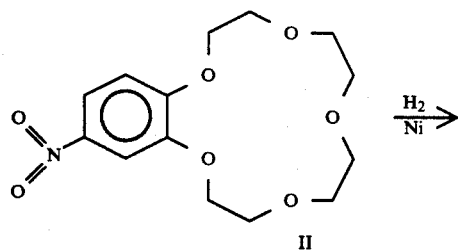

II

H₂/Ni →

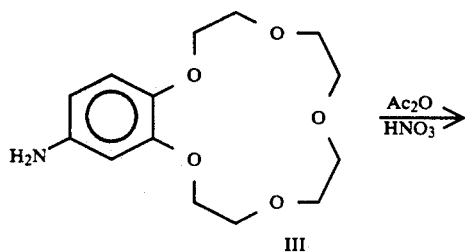

III

Ac₂O / HNO₃ →

The conversion of this compound (V) to the isocyanate (VI) was done according to the procedure of Kurite et al., *Journal of Organic Chemistry*. Vol. 41, pp. 2070–2071 (1976):

The 3-amino-4-nitrobenzo-15-crown-5 was suspended in absolute dioxane. Trichloromethyl formiate (diphosgene) was added and the reaction mixture refluxed under exclusion of moisture for 24 hours. The solvent was removed under reduced pressure and the residue crystallized from petroleum ether to get 4-nitro(15-crown-5)-3-phenylisocyanate.

V 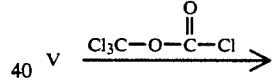 →

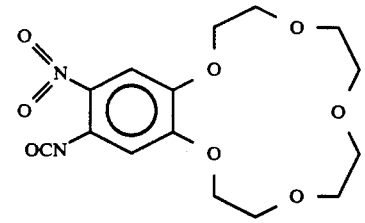

Step 2: Preparation of the bi-urethane derivative.

1-bromododecanol-12 (Aldrich 22,467-7) (VII) was converted to an ester using a procedure similar to the one described by Shigley et al., *Journal of the American Oil chemists Society*, Vol. 32, p. 213 (1955):

1-bromo-dodecanol-12 (VII) was dissolved in benzene and refluxed with acetanhydride to get 1-bromo-12-dodecylacetate (VIII). After washing with aqueous sodium carbonate solution, drying, and removing the solvent, this product was used for the following reaction.

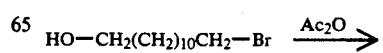

VII

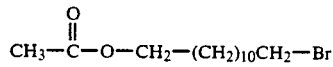

2,2'-dihydroxymethylenetetradecanol-14 (IX) was prepared according to Joshi and Bhinde, *Journal of the Indian Chemical Society*. Vol. 37, p. 461 (1960):

A sodium ethoxide solution in ethanol was refluxed for 16 hours with methyldiethylmalonate (Aldrich 12,613-6) (X) and the 1-bromo-12-dodecylacetate (VIII). Most of the ethanol was removed and the residue refluxed with aqueous potassium hydroxide for 3 hours. The solution was acidified with hydrochloric acid and a white precipitate (XI) was obtained. The precipitate was filtered and dried at 70° C. under reduced pressure for one hour. The dried precipitate was dissolved in absolute diethylester and reduced with lithium aluminum hydride to get 2,2'-dihydroxymethyl-tetradecanol(IX). 14 (IX).

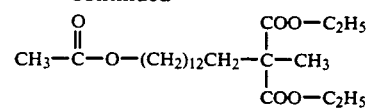

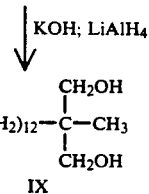

Step 3: Formation of Hydroxy-BME-44 (XII)

This is done following the procedure of Toke et al., Int. PCT Publication No. WO 83/00149:

A solution of 2,2'-dihydroxymethyltetradecanol-14 (step 2; IX) in absolute dioxane was stirred with 4-nitro-(15-crown-5)-3-phenylisocyanate (step 1; VI) for two hours at room temperature. The solvent was removed and the residue recrystallized from ethylacetate to get the 2,2'-bis-[3,4-(15-crown-5)-2-nitrophenylcarbamoxymethyl]tetradecanol-14(hydroxy-BME-44;XII).

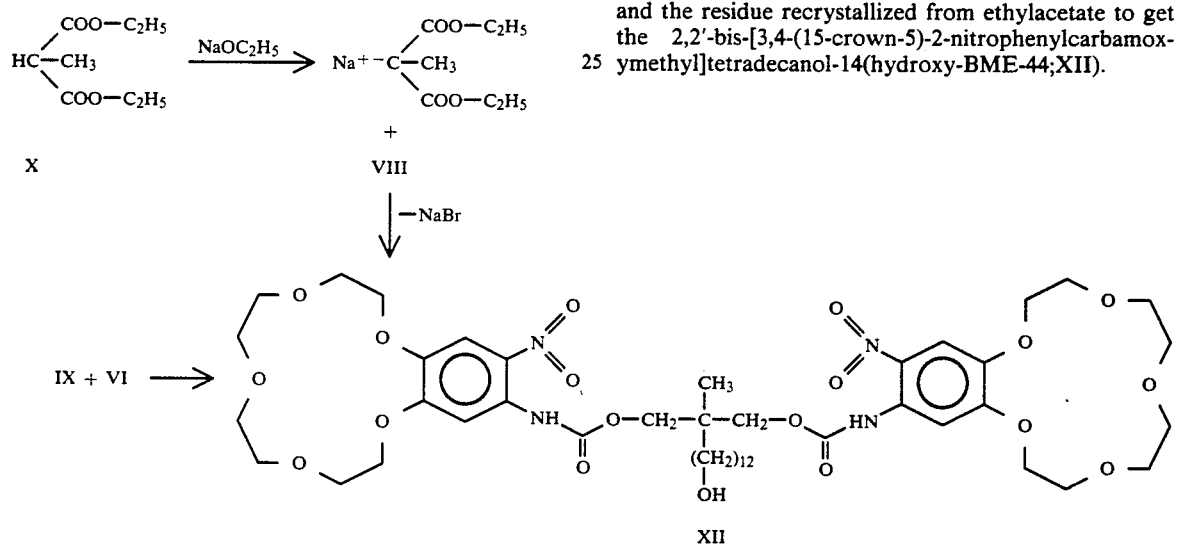

Synthesis of hydroxy-BME-44/rhodamine-B ester (XIV):

This is a well known esterification reaction: Rhodamine-B (chloride salt) (Aldrich R95-3) (XIII) and hydroxy-BME-44 (step 3; XII) were suspended in toluene and refluxed for one hour. A part of the solvent and the water formed as a reaction product were distilled off azeotropically. The ester (XIV) was recovered by crystallization at 5° C.

XIII + XII ⟶

-continued

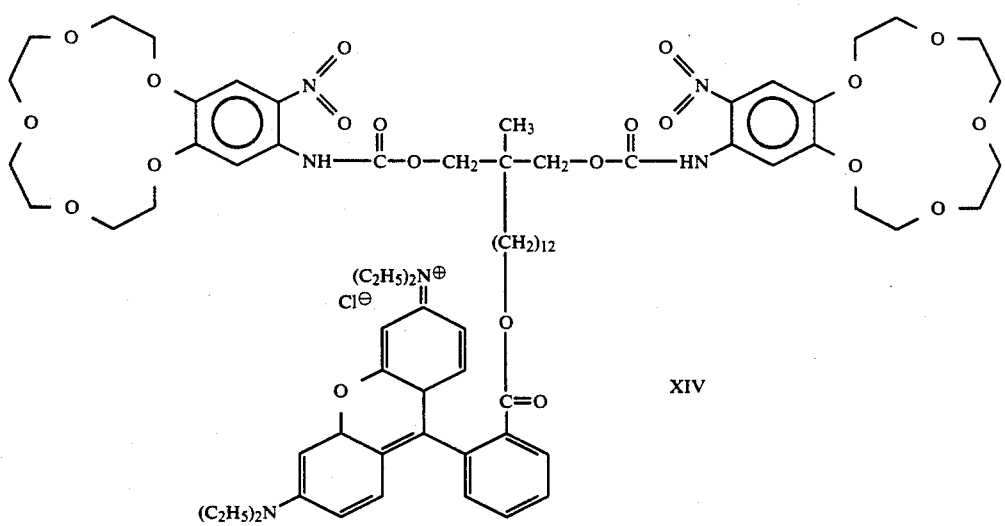

XIV

Immobilization of BME-44-Rhodamine-B ester to Polyacrylamide polymer 20 mg BME-44-Rhodamine-B ester was dissolved in isopropanol and added to a solution of 4 g aorylamide and 277 mg N,N'-methylenediacrylamide in 10 mL water. 149 mg ammonium peroxidisulfate was added and the polymerization was allowed to proceed for one hour under nitrogen. The resultant gel was washed with water to remove the excess acrylamide and with chloroform to remove the excess ester. The final product was a gel, which could be cut into various shapes and sizes for making sensors.

Description of the Fiber Optic Sensor and Optoelectronics

Figure 4:
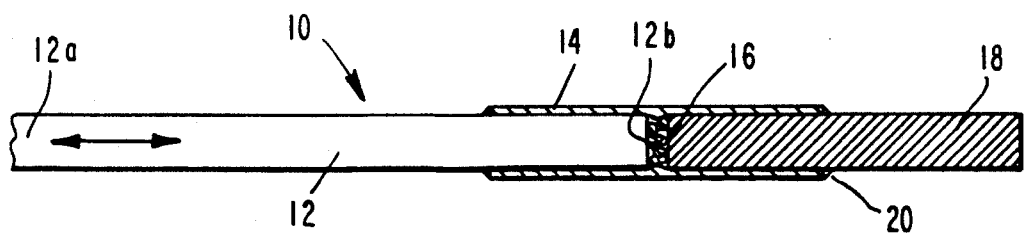
FIG. 4 is a cross-sectional view of the sensor of the invention.

FIG. 4 depicts a device in accordance with the invention, incorporating the sensor 10 of the invention. The device consists of an optical fiber 12, such as a multi-mode, step index silica fiber commonly used in communication cables. One end of the fiber 12a is connected to the optoelectronic front end (described below in reference to FIG. 5). The other end 12b of the fiber is suitably polished and inserted in a hydrophilic tubular membrane 14, such as a dialysis tubing. The tubing prevents the gel from getting into the blood and also provides support for the device.

The tubing is filled with polyacrylamide gel 16, which is synthesized as described above. Other gels, other than polyacrylamide, such as poly(hydroxymethyl ethacrylate) (poly-HEMA), may be used in the practice of the invention.

The length of the gel is adjusted to be about 100 $\mu$m, although other lengths may also be used, and a stainless steel wire 18 polished at one end is inserted in the tubing so as to act as a reflector of light coming from the optical fiber 12 and passing through the gel 16. Other metals may be used as a reflector, so long as they are biocompatible with blood.

The membrane tubing 14 is sealed to the fiber 12 at one end and to the wire 18 at the other end with an epoxy 20. Any of the well-known medical grade epoxies may be used.

Figure 5:
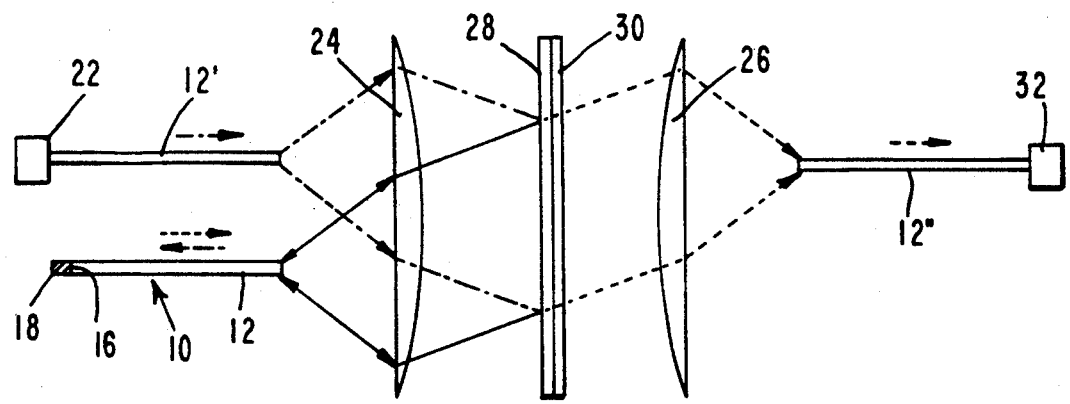
FIG. 5 is a schematic diagram of apparatus employing the sensor of the invention.

The optoelectronics is shown in FIG. 5 and consists of a source 22 of radiation, such as a light emitting diode emitting radiation at about 510 nm. This radiation is coupled from an optical fiber 12' into the optical fiber 12 by a wavelength division multiplexer. The multiplexer consists of lenses 24 and 26 and a combination of a dichroic mirror 28 and a red pass filter 30. The radiation emerging from the source 22 is collimated by the lens 24 and reflected by the dichroic mirror 28. The dichroic mirror is selected such that it reflects the radiation of wavelengths lower than 540 nm and transmits the rest.

The reflected beam is focused by the lens 24 into the sensor 10. The fluorescent radiation emitted by Rhodamine-B in the gel 16 after being excited by incoming radiation is collimated by the lens 24 onto the red pass filter 30. The filter is so chosen that it allows only the radiation of wavelengths higher than 540 nm to pass through. This radiation is collected by the lens 26 and is focused onto a detector 32 through an optical fiber 12''. The detector 32 generates a current in proportion to the intensity of the incident radiation. The magnitude of this current increases with increasing concentration of potassium in a solution to which the sensor is exposed.

The sensor of the invention is immersed in the arterial stream of the patient. The porous membrane 14 prevents large proteins and blood cells from getting into the gel 16. Most gases and all the inorganic ions (hydrated or not) easily pass through the membrane and into the gel. There is an equilibrium between the concentration of these ions in the blood stream and in the gel. Thus, by measuring the ionic concentration inside the gel, the sensor can provide information about the blood concentration of the ions. The optical fiber 12 is sufficiently long and goes all the way from the sensor to the optoelectronics front end (about 3 meters), passing through the arterial catheter.

Advantages of the Invention

The invention provides several advantages:

(1) The scheme of the invention combines the selective recognition and transduction, thereby eliminating the need for ion-selective membranes which are complex and fraught with problems of interference, and drift due to the loss of ionophore and plasticizer, etc. This is a prior art problem: In the prior art such as a potassium sensitive electrode, a membrane made of a polymer such as poly-(vinyl chloride) doped with an ionophore such as BME-44 and a plasticizer acts as a barrier to other ions, allowing only potassium ions to pass through it to the electrode for detection. Thus, the selective recognition is done by the membrane and transduction is done by the electrode. With time, the plasticizer is washed away in the contacting solution. The membrane loses its properties of ion transport and leads to a drifting signal output by the electrode.

(2) In this invention, the ionophore and the fluorophore are chemically bound to a polymer gel. This prevents the loss of either the ionophore or the dye in the course of use and therefore the sensor drift is avoided.

(3) The scheme of the invention is not diffusion-controlled and therefore results in fast responding sensors. Use of a porous membrane containing the sensing gel allows a free transport of ions in and out of the sensor. The gel itself being hydrophilic does not offer any resistance to the flow of ions. (The membrane used in the electrodes is essentially non-porous and therefore its thickness determines the response time.)

(4) The sensor does not require any electrical connection, and therefore is safe for use during electrosurgery.

INDUSTRIAL APPLICABILITY

The invention is suitably employed in the detection and determination of potassium concentration, particularly in bodily fluids.

Thus, there has been disclosed a sensor for potassium ion concentration based on fluorescent quenching. Many modifications and changes of an obvious nature will be readily apparent to one of ordinary skill in the art, and all such modifications and changes are deemed to fall within the scope of the invention as defined by the appended claims.

What is claimed is:

1. A sensor for detecting the concentration of potassium ions comprising a molecule consisting essentially of 2,2-bis(3,4-(15-crown-5)-2-nitrophenylcarboxymethyl)tetradecane which selectively complexes potassium ions, said molecule having at least one binding site and provided with a fluorophore group selected from the group consisting of Rhodamine-B, Rhodamine-110, Fluorescein, and 2,7'-dichlorofluorescein at said binding site.

2. The sensor of claim 1 wherein said binding site comprises the fourteenth carbon atom of the tetradecane moiety, to which said fluorophore group is attached.

3. The sensor of claim 1 wherein said fluorophore group consists essentially of Rhodamine-B.

4. The sensor of claim 2 wherein said molecule has an aliphatic part having a free end and said binding site is located on said free end.

5. A detector for detecting the concentration of potassium ions, said detector comprising:
    (a) a source of electromagnetic radiation;
    (b) a sensor comprising a molecule immobilized on a hydrophilic polymer, said molecule consisting essentially of 2,2-bis(3,4-(15-crown-5-2-nitrophenylcarboxymethyl)tetradecane which selectively complexes potassium ions and having at least one binding site provided with a fluorophore group selected from the group consisting of Rhodamine-B, Rhodamine-110, Fluorescein, and 2,7'-dichlorofluorescein at said binding site;
    (c) measuring means for measuring any change in intensity of said radiation passed through said sensor; and
    (d) an optical wavelength division multiplexer for directing electromagnetic radiation from said source of electromagnetic radiation to said sensor and for directing electromagnetic radiation from said sensor to said measuring means.

6. The detector of claim 5 wherein said source of electromagnetic radiation comprises a light emitting diode.

7. The detector of claim 5 wherein said binding site comprises the fourteenth carbon atom of the tetradecane moiety, to which said fluorophore group is attached.

8. The detector of claim 5 wherein said fluorophore group consists essentially of Rhodamine-B.

9. The detector of claim 5 wherein said molecule has an aliphatic part having a free end and said fluorophore is located on said free end.

10. The detector of claim 5 wherein said measuring means generates a current in proportion to the intensity of said radiation, the magnitude of said current directly proportional to the concentration of potassium ions to which said sensor is exposed.

11. The detector of claim 5 wherein said optical wavelength division multiplexer comprises a dichroic mirror for reflecting radiation of a preselected wavelength and lower and for passing wavelengths above said preselected wavelength, an optical filter for passing wavelengths above said preselected filter length, and a set of planoconvex lenses for collimating and focusing said radiation onto said sensor and onto said detector.

12. The detector of claim 11 wherein said source of electromagnetic radiator emits radiation at about 510 nm and said preselected wavelength is about 540 nm.

* * * * *